United States Patent [19]

Seneker et al.

[11] Patent Number: 4,983,763
[45] Date of Patent: Jan. 8, 1991

[54] PROCESS FOR PREPARING HIGH TRANS, TRANS-ISOMER CONTAINING 4,4'-DIISOCYANATO DICYCLOHEXYLMETHANE

[75] Inventors: Stephen D. Seneker, Paden City; Terry A. Potter; Kenneth L. Dunlap, both of New Martinsville, all of W. Va.

[73] Assignee: Mobay Corporation, Pittsburgh, Pa.

[21] Appl. No.: 511,155

[22] Filed: Apr. 19, 1990

Related U.S. Application Data

[63] Continuation-in-part of Ser. No. 468,542, Jan. 23, 1990, abandoned.

[51] Int. Cl.$^5$ .......................................... C07C 263/20
[52] U.S. Cl. ...................................... 560/352; 560/336
[58] Field of Search ................................ 560/336, 352

[56] References Cited

U.S. PATENT DOCUMENTS

| | | | |
|---|---|---|---|
| 2,494,563 | 1/1950 | Kirk, Jr. et al. | 260/563 |
| 2,606,925 | 8/1952 | Whitman | 260/563 |
| 3,153,088 | 10/1964 | Arthur | 260/563 |
| 3,155,724 | 11/1964 | Arthur | 260/563 |
| 3,384,661 | 5/1968 | Arthur | 260/563 |
| 3,393,236 | 7/1968 | Kuszewski | 260/563 |
| 3,789,032 | 1/1974 | Hoeschele | 260/75 NT |

FOREIGN PATENT DOCUMENTS

| | | |
|---|---|---|
| 961049 | 1/1975 | Canada . |
| 971184 | 7/1975 | Canada . |
| 1220715 | 1/1971 | United Kingdom . |

OTHER PUBLICATIONS

Byrne et al; A Study of Aliphatic Polyurethane Elastomers Prepared from Diisocyanate Isomer Mixtures; Rubber Chemistry and Technology; pp. 985–996, vol. 58(1985).
Wong et al; Structure–Property Relationships of Transparent Aliphatic Polyurethane Elastomers From the Geometric Isomers of Methylene BIS(4-Cyclohexyl Isocyanate); Advances in Urethane Science and Technology, vol. 9, 1984 pp. 77–101.

Primary Examiner—Joseph Paul Brust
Attorney, Agent, or Firm—Joseph C. Gil

[57] ABSTRACT

The present invention is directed to a simple process for preparing a 4,4'-diisocyanato dicyclohexylmethane containing at least 90% by weight of the trans, trans-isomer. More particularly, the process comprises:

(a) melting a mixture of 4,4'-diisocyanato dicyclohexylmethane isomers containing at least 30% by weight, and preferably from 45 to 55% by weight, of the trans,trans-isomer,
(b) cooling the melted mixture to a temperature of from about 20° to about 25° C. to form;
   (1) a liquid phase which contains from about 18 to about 25% by weight of the trans,trans-isomer, and
   (2) a solid phase which contains from about 70 to about 85% by weight of the trans,trans-isomer,
(c) removing said liquid phase,
(d) dissolving said solid phase in a solvent to form a 4,4'-diisocyanato dicyclohexylmethane-containing solution,
(e) allowing said solution to remain at room temperature for a time sufficient to form:
   (1) a solid phase containing at least 90% by weight, and preferably at least 98% by weight of the trans,trans-isomer, and
   (2) a liquid phase containing said solvent and a mixture of 4,4'-diisocyanato dicyclohexylmethane isomers containing from 30 to 70% by weight, and preferably from 45 to 55% by weight of the trans,trans-isomer, and
(f) removing said solid phase (e)(1).

3 Claims, No Drawings

PROCESS FOR PREPARING HIGH TRANS, TRANS-ISOMER CONTAINING 4,4'-DIISOCYANATO DICYCLOHEXYLMETHANE

CROSS-REFERENCE TO RELATED APPLICATION

This application is a continuation-in-part of U.S. application Ser. No. 07/468,542, filed on Jan. 23, 1990, now abandoned.

BACKGROUND OF THE INVENTION 4,4'-diisocyanato dicyclohexylmethane ("PICM") is a cycloaliphatic diisocyanate of low volatility. PICM and other aliphatic isocyanates are useful in the preparation of non-discoloring polyurethanes. In general, such isocyanates are reacted with glycols and/or polyols and chain extenders and/or cross linkers. Such isocyanates are particularly useful in the preparation of polyurethane coatings and elastomers.

PICM and the diamine precursor, 4,4'-diamino dicyclohexylmethane ("PACM"), exist in three stereoisomeric forms (i.e., trans,trans; cis,trans; and cis,cis) as described, for example, in U.S. Pat. Nos. 2,606,925, and 3,789,032, Canadian Pat. Nos. 961,049 and 971,184, and British Pat. No. 1,220,715. Commercial grades of PACM normally contain all three isomers.

The most direct method of producing PICM is to first hydrogenate diamino diphenylmethane to form a mixture of the stereoisomers of PACM, and to then phosgenate the mixture. When the synthesis of PICM is conducted using readily available mixtures of stereoisomers of PACM (such as the equilibrium mixture described in U.S. Pat. No. 3,155,724), the PICM obtained is a solid at normal operating temperatures, having a melting point of about 58° C., which corresponds to a trans,trans-isomer content of about 54%. Various PICM mixtures are known in the art which have trans,trans-isomer contents of from about 17 to about 55% by weight. In addition, the art has recognized an advantage in utilizing high trans,trans-isomer PICM in producing elastomers (see, U.S. Pat. No. 3,789,032).

In order to prepare PICM of relatively high trans,trans-isomer content, the art has generally used a PACM having a relatively high trans,trans-isomer content in the phosgenation reaction. Various methods are known for treating PACM to obtain the requisite high trans,trans-isomer content. Crystallization techniques have been described in the art. See, e.g., U.S. Pat. Nos. 2,494,563, 3,153,088, 3,384,661 and 3,393,236. The crystallization of PACM suffers from various disadvantages. PACM readily forms a precipitant when exposed to carbon dioxide, causing problems in filtering and contamination of the crystals (see, U.S. Pat. No. 2,494,563, column 3, lines 26-29, and column 4, lines 72-75). In addition, PACM is generally difficult to crystallize since it will easily form a supercooled liquid. The prior art has overcome this problem by adding seed crystals (U.S. Pat. No. 2,494,563), by lowering the viscosity by using an inert solvent (U.S. Pat. Nos. 2,494,563, 3,153,088, 3,393,236 and 3,384,661), or by forming an adduct of PACM that crystallizes better, such as the hydrate (U.S. Pat. No. 3,153,088) or the alcoholate (U.S. Pat. No. 3,384,661). Such an adduct must be treated to remove water or alcohol before phosgenating to PICM.

It is known to separate the trans,trans-isomer from industrial mixtures of PICM (with a trans,trans content of from 17% to 24%) by fractional crystallization followed by vacuum distillation. The liquid mixture was cooled to 10° C. until crystallization took place and the solid fraction (the trans,trans-isomer) was removed by filtration in a nitrogen atmosphere. The residue was washed with cold hexane and stored under a nitrogen atmosphere. The filtrate was recooled and any new solids removed. See, Byrne et al, "A Study of Aliphatic Polyurethane Elastomers Prepared From Diisocyanate Isomer Mixtures," *Rubber Chemistry and Technology*, vol. 58, 1985, pages 985-996, and Wong et al, "Structure-Property Relationships of Transparent Aliphatic Polyurethane Elastomers From the Geometric Isomers of Methylene bis(4-Cyclohexyl Isocyanate)," *Advances in Urethane Science and Technology*, vol. 9, 1984, pages 77-101. This method suffers from two disadvantages. First, the yield of the trans,trans isomer is poor. Secondly, cooling below ambient temperature is an expensive process on an industrial scale.

DETAILED DESCRIPTION OF THE INVENTION

The present invention is directed to a relatively simple process for preparing a PICM containing a relatively high amount of the trans,trans-isomer, which process overcomes the problems associated with the prior art. More particularly, the present invention is directed to a process for the preparation of a 4,4'-diisocyanato dicyclohexylmethane containing at least 90% by weight, and preferably at least 98% by weight, of the trans,trans isomer comprising:

(a) melting a mixture of 4,4'-diisocyanato dicyclohexylmethane isomers containing at least 30% by weight, and preferably from 45% to 55% by weight, of the trans,trans isomer, (b) cooling the melted mixture to a temperature of from about 20° C. to about 25° C. to form:
   (1) a liquid phase which contains from about 18% to about 25% by weight of the trans,trans isomer, and
   (2) a solid phase which contains from about 70% to about 85% by weight of the trans,trans isomer, (c) removing said liquid phase (which is a commercially viable product), (d) dissolving said solid phase in a solvent to form a 4,4'-diisocyanato dicyclohexylmethane-containing solution, (e) allowing said solution to remain at room temperature for a time sufficient to form:
   (1) a solid phase containing at least 90% by weight, and preferably at least 98% by weight of the trans,trans isomer, and
   (2) a liquid phase containing said solvent and a mixture of 4,4'-diisocyanato dicyclohexylmethane isomers containing from 30% to 70% by weight, and preferably from 45% to 55% by weight of the trans,trans isomer, and (f) removing said solid phase (e)(1).

In the most preferred embodiment, the solvent is removed from the liquid phase (e)(2) and returned to step (d), and the residue remaining after the solvent removal is returned to step (a).

Substantially any mixture of PICM containing at least 30% by weight, and preferably containing from 45% to 55% by weight, of the trans,trans isomer can be used in step (a) of the process of the invention. It is generally preferable to utilize commercially available mixtures which typically contain about 50% by weight of the trans,trans isomer. The particular mixture selected is melted, typically by heating to a temperature of from 60° C. to 90° C. for a period of from 60 to 120 minutes. The melted mixture is then cooled to a temperature of from about 20° C. to about 25° C. to form liquid and solid phases having the trans,trans isomer contents noted above. Typically, the melt is cooled to the requisite temperature in from 180 to 360 minutes, and is held at that temperature for from 120 to 360 minutes.

The liquid and solid phases formed by cooling the melt can be separated by substantially any technique known in the art, such as, for example, filtration, decanting, centrifugation or the like. Once the two phases are separated, the solid phase is then dissolved in an appropriate solvent. Useful solvents include hydrocarbons such as cyclohexane, heptane and hexane; aromatic solvents such as toluene; ketones such as methylethyl ketone, methylisobutyl ketone and acetone; esters such as ethyl acetate and butyl acetate; ethers such as diethyl ether; and chlorine containing solvents such as monochlorobenzene. Cyclohexane is the presently preferred solvent. In general, the amount of solvent used ranges from 10% to 30% by weight based on the total weight of the PICM and the solvent. Of course, higher amounts of solvent could be used, but the overall yield would be reduced.

Once the PICM is dissolved in the solvent, the resultant solution is allowed to remain at room temperature (typically from 20° C. to 25° C.) for a time sufficient to form two phases having the trans,trans isomer content noted under step (e) above. In general, a time of from 60 to 360 minutes at room temperature is sufficient to allow formation of the two phases. The two phases can then be separated by substantially any technique known in the art. It is presently preferred to remove the solids using vacuum filtration and to remove any residual solvent by either heating under an appropriate vacuum, or by spin drying.

The invention is further illustrated but is not intended to be limited by the following examples in which all parts and percentages are by weight unless otherwise specified.

EXAMPLES

Example 1 - Steps (a) through (c)

4000 parts of a 4,4'-diisocyanato dicyclohexylmethane containing 50% by weight of the trans,trans isomer were charged to a 1 gallon glass jar and completely melted at 80° C. The melt was then allowed to cool to room temperature (22° C.) and kept at that temperature for 16 hours. The liquid and solid phases were separated at room temperature by simply inverting the jar and decanting the liquid phase. The liquid phase contained 19.9% by weight of the trans,trans isomer, while the solid phase contained 75.2% by weight of the trans,-trans isomer. The weight percent yields of liquid and solid phases were 48% and 52% respectively.

Example 2 - Steps (d) through (f)

To 180 parts of the solid phase of Example 1 were added 20 parts (10% by weight based on the combined weight of the solid and solvent) of cyclohexane. The mixture was heated to 70° C. to achieve solubility and then allowed to cool to room temperature (22° C.). The solution was kept at room temperature for 24 hours. The solids were then vacuum filtered and the residual cyclohexane removed by heating under a vacuum (1mm Hg.) for 6 hours. The composition of the solid contained 91.9% by weight of the trans,trans isomer. The weight percent yield with respect to the 180 parts of the solid phase of Example 1 was 78%. A repeat of the Example 2 using the 91.9% trans,trans content product resulted in a solid phase containing 98.8% of the trans,trans isomer and a weight percent yield of 74% based on the 180 parts of the solid phase of Example 1.

Example 3 - Steps (d) through (f)

To 160 parts of the solid phase of Example 1 were added 40 parts (20% by weight based on the combined weight of the solid and solvent) of cyclohexane. The mixture was heated to 70° C. to achieve solubility and then allowed to cool to room temperature (22° C.). The solution was kept at room temperature for 24 hours. The solids were then vacuum filtered and the residual cyclohexane removed by heating under a vacuum (1 mm Hg.) for 6 hours. The composition of the solid contained 98.1% by weight of the trans,trans isomer. The weight percent yield with respect to the 160 parts of the solid phase of Example 1 was 75%. A repeat of the Example 3 using the 98.1% trans,trans content product resulted in a solid phase containing 99.8% of the trans,trans isomer and a weight percent yield of 64% based on the 160 parts of solid phase of Example 1.

Example 4 - Steps (d) through (f)

To 140 parts of the solid phase of Example 1 were added 60 parts (30% by weight based on the combined weight of the solid and solvent) of cyclohexane. The mixture was heated to 70° C. to achieve solubility and then allowed to cool to room temperature (22° C.). The solution was kept at room temperature for 24 hours. The solids were then vacuum filtered and the residual cyclohexane removed by heating under a vacuum (1 mm Hg.) for 6 hours. The composition of the solid contained 98.9% by weight of the trans,trans-isomer. The weight percent yield with respect to the 140 parts of the solid phase of Example 1 was 58%. A repeat of the Example 4 using the 98.9% trans,trans content product resulted in a solid phase containing 99.9% of the trans,trans-isomer and a weight percent yield of 49% based on 140 parts of solid phase of Example 1.

What is claimed is:

1. A process for the preparation of a 4,4'-diisocyanato discylohexylmethane containing at least 90% by weight of the trans,trans-isomer comprising:
   (a) melting a mixture of 4,4'-diisocyanato dicyclohexylmethane isomers containing at least 30% by weight of the trans,trans-isomer,
   (b) cooling the melted mixture to a temperature of from about 20° C. to about 25° C. to form:
     (1) a liquid phase which contains from about 18 to about 25% by weight of the trans,trans-isomer, and
     (2) a solid phase which contains from about 70% to about 85% by weight of the trans,trans-isomer,
   (c) removing said liquid phase,
   (d) dissolving said solid phase in a solvent to form a 4,4'-diisocyanato discyclohexylmethane-containing solution,
   (e) allowing said solution to remain at room temperature for a time sufficient to form:
     (1) a solid phase containing at least 90% by weight of the trans,trans-isomer, and
     (2) a liquid phase containing said solvent and a mixture of 4,4'-diisocyanato dicyclohexylmethane isomers containing from 30% to 70% by weight of the trans,trans-isomer, and
(f) removing said solid phase (e)(1).

2. The process of claim 1 wherein the mixture of step (a) contains from 45% to 55% by weight, of the trans,-trans-isomer, wherein the solid phase of step (e) contains at least 98% by weight of the trans,trans isomer, and wherein the liquid phase of step (e) contains said solvent and a mixture of 4,4'-diisocyanato dicyclohexylemethane isomers containing from 45% to 55% by weight of the trans,trans-isomer.

3. The process of claim 1, further comprising the steps of (g) removing said solvent from said liquid phase (e)(2) and returning the solvent so removed to step (d), and (h) returning the residue remaining after the solvent removal step (g) to step (a).

* * * * *